(12) United States Patent
Teague (10) Patent No.: US 10,956,031 B1
(45) Date of Patent: Mar. 23, 2021

(54) GRAPHICAL USER INTERFACE FOR DATA ENTRY INTO AN ELECTRONIC HEALTH RECORDS APPLICATION

(71) Applicant: Allscripts Software, LLC, Raleigh, NC (US)

(72) Inventor: Ross Teague, Cary, NC (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 0 days.

(21) Appl. No.: 16/435,047

(22) Filed: Jun. 7, 2019

(51) Int. Cl.
  *G06F 3/0488* (2013.01)
  *G16H 10/60* (2018.01)
  *G06F 40/174* (2020.01)

(52) U.S. Cl.
  CPC ...... *G06F 3/04883* (2013.01); *G06F 3/04886* (2013.01); *G06F 40/174* (2020.01); *G16H 10/60* (2018.01)

(58) Field of Classification Search
  CPC .............. G06F 3/04883; G06F 40/174; G06F 3/04666; G16H 10/60
  USPC ........................................................ 715/268
  See application file for complete search history.

(56) References Cited

U.S. PATENT DOCUMENTS

| | | | |
|---|---|---|---|
| 5,063,600 A * | 11/1991 | Norwood | G06F 3/033 345/173 |
| 5,604,516 A | 2/1997 | Herrod et al. | |
| 7,190,351 B1 | 3/2007 | Goren | |
| 8,009,146 B2 | 8/2011 | Pihlaja | |
| 9,116,615 B2 | 8/2015 | Ng et al. | |
| 2001/0016856 A1* | 8/2001 | Tsuji | G06F 3/043 715/222 |
| 2003/0193481 A1* | 10/2003 | Sokolsky | G06F 3/0488 345/173 |
| 2006/0209044 A1* | 9/2006 | Cohen | G06K 9/222 345/173 |
| 2006/0245641 A1* | 11/2006 | Viola | G06F 40/295 382/155 |
| 2006/0267965 A1* | 11/2006 | Clary | G06F 3/03545 345/179 |
| 2013/0057475 A1 | 3/2013 | Duggan et al. | |
| 2013/0120271 A1 | 5/2013 | Lee et al. | |
| 2014/0321751 A1* | 10/2014 | Okamoto | G06K 9/00402 382/189 |

(Continued)

*Primary Examiner* — Stephen S Hong
*Assistant Examiner* — Broderick C Anderson
(74) *Attorney, Agent, or Firm* — Medley, Behrens & Lewis, LLC (57) ABSTRACT

A client EHR executing on a client computing device is described herein, wherein the client EHR is configured to present a GUI on a display of the client computing device. The GUI comprises a first field, a second field, and a third field, wherein the first field is configured to receive an identifier for a category of clinical data, the second field is configured to receive clinical data of the identified category of clinical data and the third field is configured to present the identified category of clinical data from the electronic health record of a patient. The client computing device then receives input comprising clinical data of the category identified, which is then integrated into the patient's electronic health record maintained by the EHR. After receiving an input comprising clinical data, the GUI automatically advances to the next subcategory of the identified category for which clinical data is needed.

20 Claims, 10 Drawing Sheets

(56) References Cited

U.S. PATENT DOCUMENTS

2015/0193141 A1* 7/2015 Goldsmith ............. G06K 9/222
                                                         345/173
2016/0371246 A1* 12/2016 Deepak ................. G06F 40/186

* cited by examiner

GRAPHICAL USER INTERFACE FOR DATA ENTRY INTO AN ELECTRONIC HEALTH RECORDS APPLICATION

BACKGROUND

Electronic health record applications (EHRs) are computer-executable applications utilized in healthcare environments. EHRs are generally configured to perform various tasks related to healthcare including health record maintenance tasks, patient intake tasks, scheduling tasks, insurance processing tasks, billing tasks, and so forth. EHRs are often used by healthcare workers at the point of care (i.e., at a time when the healthcare worker is providing care to a patient). For example, a healthcare worker (e.g., a physician) may retrieve clinical data from a patient record maintained by an EHR to relatively quickly ascertain problems being experienced by the patient, medications currently taken by the patient, and so forth.

To generate a complete patient record, clinical data must be collected and input into the patient record. As such, clinical data is typically collected during patient intake and during an appointment. A variety of methods for recording the clinical data and eventually migrating it to an EHR have been developed over time, some computer-executable and some paper-based. For example, the clinical data is collected by asking the patient questions and taking measurements (e.g., temperature, blood pressure, weight, height, etc.) or performing tests. The collected clinical data can then be written down and input into an EHR at a later time, or the healthcare worker can input the clinical information directly into the EHR by way of a computing device as the clinical data is collected.

There are various deficiencies associated with conventional EHR data entry. First, conventional EHRs are not configured to allow for easy maneuvering through interfaces to a specific type of clinical data, which makes data entry more time consuming as the EHR is programmed to collect clinical data in a specific order, which may not match the order that the healthcare worker actually takes measurements, performs tests, etc. Second, even when conventional EHRs are configured to allow a healthcare worker to advance through interfaces for entering clinical data in a certain order according to the healthcare worker's work flow, the EHR is not configured to receive the data input in a manner that allows for natural engagement between the healthcare worker and the patient. Rather, the clinical data is input either using a keyboard or, in the case of a touch-screen computing device such as a tablet or smartphone, requires two hands for data entry. Accordingly, the healthcare worker tends to look at a screen or keyboard when talking to the patient, rather than looking at the patient. Third, data entry methods of conventional EHRs do not allow for automatic advancement to the next data point for which data must be entered.

SUMMARY

The following is a brief summary of subject matter that is described in greater detail herein. This summary is not intended to be limiting as to the scope of the claims.

Described herein are various technologies pertaining to an electronic health record application (EHR) that is configured to receive data input. More specifically, a computer-executable client EHR application executing on a client computing device is described herein, wherein the client EHR is configured to present a graphical user interface (GUI) on a display of the client computing device. In an exemplary embodiment, the client EHR receives input from a healthcare worker that identifies a patient. The input may be set forth by the healthcare worker in connection with retrieving, by way of the client EHR, data pertaining to the patient. The client computing device transmits the input to a server computing device that executes a server EHR, wherein the server EHR is configured to generate search results based on the input and transmit such search results to the client computing device.

Responsive to receiving the search results, the client computing device displays a GUI for the client EHR on the display of the client computing device. The GUI comprises a plurality of fields. The plurality of fields include a first field that is configured to receive a handwritten identifier (e.g., by a thumb of a healthcare worker over a touch-sensitive screen or a stylus used by the healthcare worker over a touch-sensitive screen) that identifies a category of clinical data that is to be entered by the healthcare worker, a second field that is configured to receive handwritten input comprising clinical data of the category of clinical data identified by the healthcare worker, and a third field that displays the patient's electronic health record.

When the client computing device receives a first handwritten input identifying a category of clinical data in the second field, the client computing device displays, by way of the GUI, the clinical data assigned to the category within the patient's electronic health record (in the first field of the GUI). The category of clinical data can have several sub-categories or types of clinical data. For example, in response to the healthcare worker entering the first handwritten input that identifies the category "Vitals" into the second field, the client computing device causes the patient's vitals history to be displayed in the first field of the GUI. The patient's vitals history comprises several sub-categories of clinical data such as "body temperature", "blood pressure", "pulse", amongst other, and these sub-categories can have a pre-defined order within the broader "Vitals" category. Once the healthcare worker provides the first handwritten input "Vitals" in the first field, the client computing device then receives second handwritten input provided by the healthcare worker in the second field of the GUI, wherein the second handwritten input comprises clinical data assigned to a first sub-category in the predefined order. The server EHR, upon receiving the first handwritten input and the second handwritten input from the client EHR, integrates the clinical data into the patient's electronic health record maintained by the server EHR. After the server EHR integrates the clinical data into the sub-category of the patient's electronic health record, the client EHR automatically advances the GUI to a next sub-category in the predefined order in the electronic health record of the "Vitals" category. The client EHR then receives, at the second field, a third handwritten input, comprising clinical data, to be integrated into the next sub-category location in the patient electronic health record of the "Vitals" category.

In an exemplary embodiment, the client computing device is configured with a touch-screen display such that the first field and second field are free-hand data entry fields that are positioned in a corner of the GUI where the first field is positioned above the second field in the corner, while the third field presents portion(s) of the electronic health record of the patient. Positioning the data entry fields together in a single corner allows for the healthcare worker to enter data into the GUI without requiring the healthcare worker to move his or her hand along the bezel of the client computing device, thereby reducing movement of hands and/or fingers when compared to movement of hands and/or fingers required using conventional approaches. For example, tests have indicated a 15% reduction in time required to enter data using the approach described herein when compared to conventional approaches. The client computing device can also optionally be configured to receive input via a keyboard presented on the touchscreen display for longer entries such as clinical notes.

The client EHR can be configured to automatically display categories of clinical data in a particular order that follows a healthcare worker's work flow. For example, if a healthcare worker typically enters vitals first, then proceeds to entering family history, followed by review of systems, the client EHR can be configured to present screens that allow for data entry in that order. Another healthcare worker may enter family history first, then proceed to vitals, followed by review of systems. The client EHR can be configured by the healthcare worker to present screens that allow for data entry review in the order of his or her work flow to reduce time spent navigating between interfaces manually.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Various technologies pertaining to a GUI for a client electronic health record application (EHR) are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Figure 1:
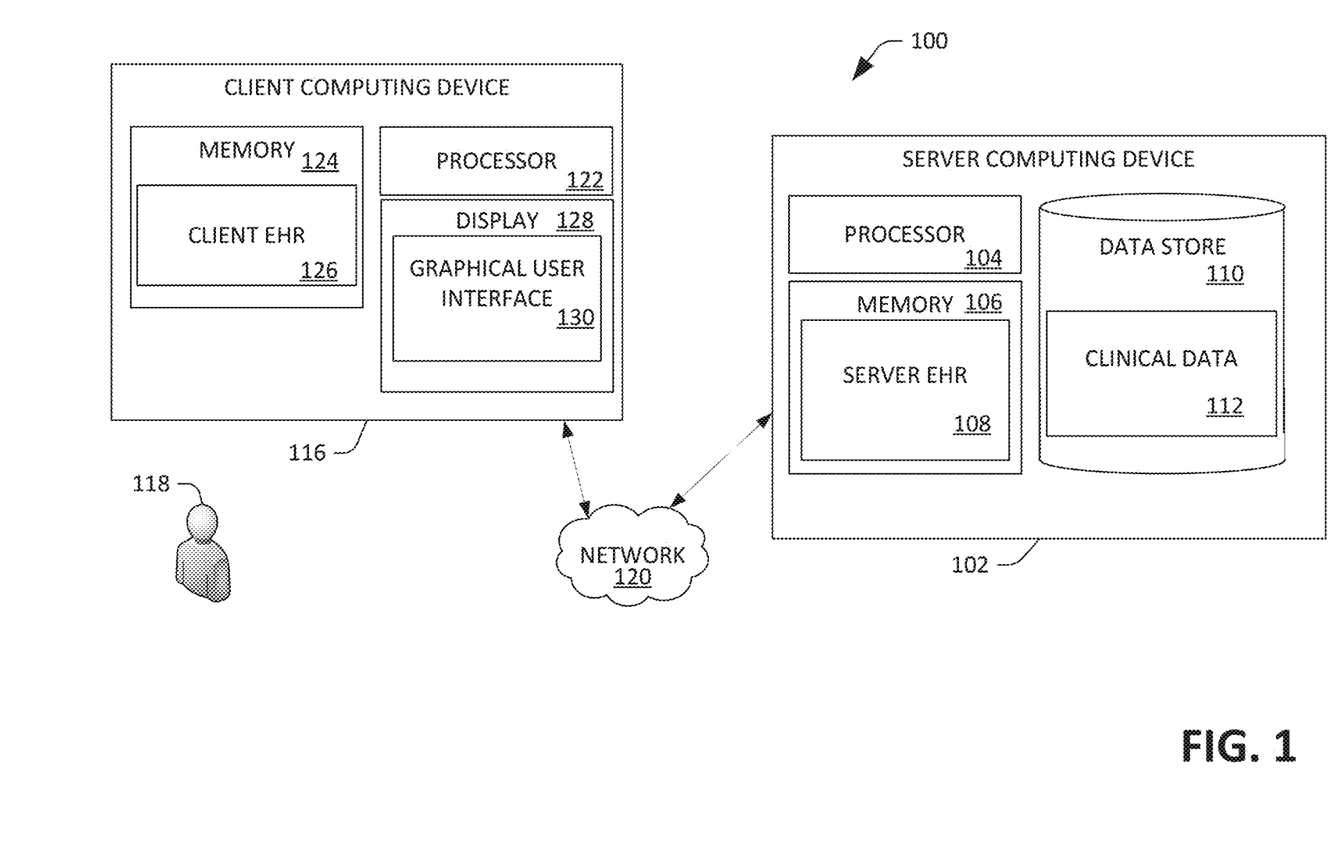
FIG. 1 is a functional block diagram of an exemplary computing system that facilitates data entry at a GUI within a client EHR.

With reference to FIG. 1, an exemplary system 100 that facilitates presenting a data entry GUI for a client EHR is illustrated. The system 100 includes a server computing device 102 comprising a processor 104 and memory 106, wherein the memory 106 has a server EHR 108 loaded therein. The server EHR 108 is configured to perform a variety of tasks related to patient care (e.g., patient intake, prescription generation, patient record creation and maintenance, etc.). The server computing device 102 also includes a data store 110 that comprises clinical data 112 about patients, wherein the clinical data 112 is maintained by the server EHR 108.

By way of example, the clinical data 112 can include electronic health records, claims data, patient/disease registries data, health surveys data, and/or clinical trials data. For instance, electronic health records include, but are not limited to including, data pertaining to administrative and demographic information, diagnosis, treatment, patient/disease registries, prescription drugs, laboratory tests, physiological monitoring data, hospitalization, patient insurance, etc. Administrative information includes hospital discharge data. Demographic information includes identifying information, vitals, etc. Diagnosis and treatment data include a patient's health history regarding previous ailments and any treatments received for those ailments. Patient/disease registries data includes data generated by clinical information systems that track data for certain chronic conditions, such as Alzheimer's Disease, cancer, diabetes, heart disease, and asthma.

Clinical data 112 can further include data of several different categories of data, such as vitals, family history, review of systems, nervous systems, renal system, reproductive system, etc. Each category of data can include one or more sub-categories of data. For example, the "vitals" category may include blood pressure, pulse, body temperature, etc. As will be described in greater detail below, each category can be assigned a shorthand identifier—for instance, the category "vitals" can be assigned the identifier "V", the category "family history" can be assigned the identifier "FH", and so forth. Thus, each identifier is a relatively small number (e.g., one or two) of alphanumerical characters. Still further, optionally, sub-categories can be assigned identifiers.

The system 100 further includes a client computing device 116 that is operated by a healthcare worker 118 and is in network communication with the server computing device 102 by way of a network 120 (e.g., Internet, intranet, etc.). The client computing device 116 comprises a processor 122 and memory 124, wherein the memory 124 has a client EHR 126 loaded therein. In general, the client EHR 126 is configured to interface with the server EHR 108 executing on the server computing device 102 to provide access to healthcare-related data to the healthcare worker 118 and to update healthcare records. The client computing device 116 includes a touchscreen display 128, wherein the display presents a graphical user interface (GUI) 130 of the client EHR 126.

The GUI 130 includes a first field that is configured to receive an identifier of a category (or sub-category) of clinical data, a second field that is configured to receive data that is to be assigned to the category (and sub-category) of the clinical data, and a third field that is configured to present data to the healthcare worker 118. For instance, the "vitals" category of clinical data can be assigned an identifier of "V", a "family history" category of clinical data can be assigned an identifier of "FH", etc. Therefore, when the first field of the GUI receives an identifier "V", the client EHR presents the patient's vitals on the GUI. Similarly, when the first field of the GUI receives input comprising "FH", the client EHR presents the patient's family history on the GUI. Furthermore, an identifier can be assigned to integrate frequently used clinical notes that, when the input is entered, cause the clinical note to automatically integrate into the EHR. For example, if a patient is diagnosed with depression and is prescribed a medication to treat the depression, an identifier can be entered by the healthcare worker 118 wherein the identifier is assigned to a clinical note indicating the healthcare worker 118 reviewed medication instructions, medication risks, etc. of the medication he is prescribing with the patient. In this example, the identifier could be "RxΣ" and upon receipt of input comprising that identifier, the client EHR causes a clinical note reading: "Prescribed Patient a new medication after discussing symptoms with patient. I explained the benefits of the medication as well as the risks. Patient confirmed patient understood the major side-effects. I went on to review dosage instructions and Patient confirmed that Patient understood when and how to take the medication. Patient was instructed to call me immediately upon noticing any adverse side-effects. I will check in with patient in thirty days to see how the medication is working."

Exemplary operation of the system 100 is now set forth. The client computing device 116 can receive user credentials from the healthcare worker 118 and can transmit the user credentials to the server computing device 102 for authentication. The server EHR 108 can authenticate the healthcare worker 118, based upon the user credentials, and can provide the healthcare worker 118 with access to functionality of the server EHR 108 via the client EHR 126 executing on the client computing device 116.

The client computing device 116 receives a patient identifier set forth by the healthcare worker 118 by way of the client EHR 126. The patient identifier can be indicative of at least one patient. In a non-limiting example, the input can be one or more of a first name, a last name, an address, a telephone number, a patient identification number, a social security number, or another type of information for identifying the patient. Furthermore, the input need not be a complete term. For example, the input can be one or more of part of a first name, part of a last name, part of a social security number, etc. Responsive to receiving the input from the healthcare worker 118, the client computing device 116 transmits the input to the server computing device 102 by way of the network 120.

The server computing device 102 receives the input from the client computing device 116 comprising the patient identifier. Responsive to receiving the input, the server computing device 102 executes a search over the clinical data 112 for an electronic health record indexed to the patient identifier. The server computing device 102 then returns as search results the electronic health records of the patient identified by the patient identifier. Responsive to generating the search results, the server computing device 102 can transmit the search results to the client computing device 116 by way of the network 120.

The client EHR 126 receives at least a portion of the electronic health record from the server computing device 102. Responsive to receiving the electronic health record, the client EHR 126 presents the GUI 130 on the touchscreen display 128 of the client computing device 116. Upon receipt of the patient identifier and receiving the electronic health record from the server EHR 108, the first field receives an identifier for a category from the healthcare worker 118 via the touchscreen display 128.

Subsequently, the second field receives clinical data of a subcategory of the category identified in the first field. For example, if the identifier received by the first field identifies "Vitals" as the category of data, the second field is configured to receive input comprising a subcategory of "Vitals" information such as blood pressure, pulse, etc. In a non-limiting example, when the second field receives input comprising "120/90 BP", the electronic health record is automatically updated to indicate that the patient has a blood pressure of 120/90, and the healthcare worker 118 need not indicate that the clinical data being entered is a blood pressure reading. Further details may then be entered such as whether the blood pressure reading was taken with the patient standing or sitting, as well as additional clinical notes.

Responsive to receiving the subcategory of clinical data of the identified category, the client EHR 126 updates the GUI 130 to include the newly entered clinical data as well as presenting a plurality of fields representing the remaining subcategories of the identified category, while the second and third fields remain displayed in the GUI 130. In addition, field A in the plurality of fields is automatically selected by the client EHR 126, and the healthcare worker 118 sets forth clinical data (e.g., 120/90 BP), and then sets forth a data entry command (e.g., a tap on a touchscreen). Upon the client EHR 126 detecting the data entry command, the client EHR 126 recognizes the clinical data in the second field and populates field A with the clinical data in ASCII format, for example. Once the client EHR 126 detects the data entry command, the client EHR 126 automatically advances to field B. This process can continue until all sub-category fields in a category of clinical data are filled, at which point the client EHR 126 can then automatically advance to a next category of clinical data.

In an embodiment, if the healthcare worker 118 does not wish to set forth the clinical data belonging to a category for a page of the EHR being presented on the display 128, the healthcare worker 118 can provide a command that causes the client EHR 126 to advance to the next category of clinical data programmed into the EHR. For example if the next category of clinical data programmed to appear is not the healthcare worker's 118 next category of clinical data in his or her workflow, the healthcare worker 118 can input an identifier for a different category of clinical data input the first field of the GUI 130, which will cause the client EHR 126 to update the GUI 130 to present the desired category of clinical data. For example, if the programmed order of categories of clinical data is "Vitals" followed by "Review of Systems" then "Family History", but the healthcare worker 118 personally prefers to proceed from "Vitals", to "Family History", then "Review of Systems", the healthcare worker 118 can input the identifier for "Family History" (e.g., FH) into the first field and the client EHR 126 updates the GUI 130 to present "Family History" as the next category of clinical data. Upon receiving input from the healthcare worker 118 at the second field of the GUI 130 comprising clinical data for the patient, the client EHR 126 transmits the clinical data to the server EHR 108 for storage in the data store 110.

In an embodiment, the client EHR 126 executing on the client computing device 116 can be configured to minimize the first field and second field upon receipt of a command set forth by the healthcare worker 118 by way of the GUI 130. Minimizing the first field and second field of the GUI 130 allows for increased visibility of content of the electronic health record of the patient being presented in the third field of the GUI 130. Upon receipt of a second command, the first field and second field are restored to their initial positions on the GUI 130.

In an embodiment, the client computing device 116 can also optionally be configured to receive input via a keyboard, presented on the touchscreen display 128, for longer entries such as clinical notes. The client EHR 126 can receive input indicating that a keyboard is preferred in the GUI instead of the first field and second field. In that case, the first field and the second field are minimized, and a keyboard is displayed on the GUI 130 presented on the touchscreen display 128. Responsive to receipt of an additional input, the GUI 130 is updated to display the first field and the second field as opposed to the keyboard. A user is able to cause the GUI 130 to display the keyboard or the first and second fields when desired.

The system 100 provides various advantages over conventional approaches to inputting clinical data at the point of care. First, the system 100 enables a healthcare worker to minimize time spent inputting information by decreasing the amount of movement required to navigate a GUI. Second, the system 100 enables a healthcare worker to examine relevant clinical details about a patient more quickly than in conventional client EHR searching interfaces.

Figure 2:
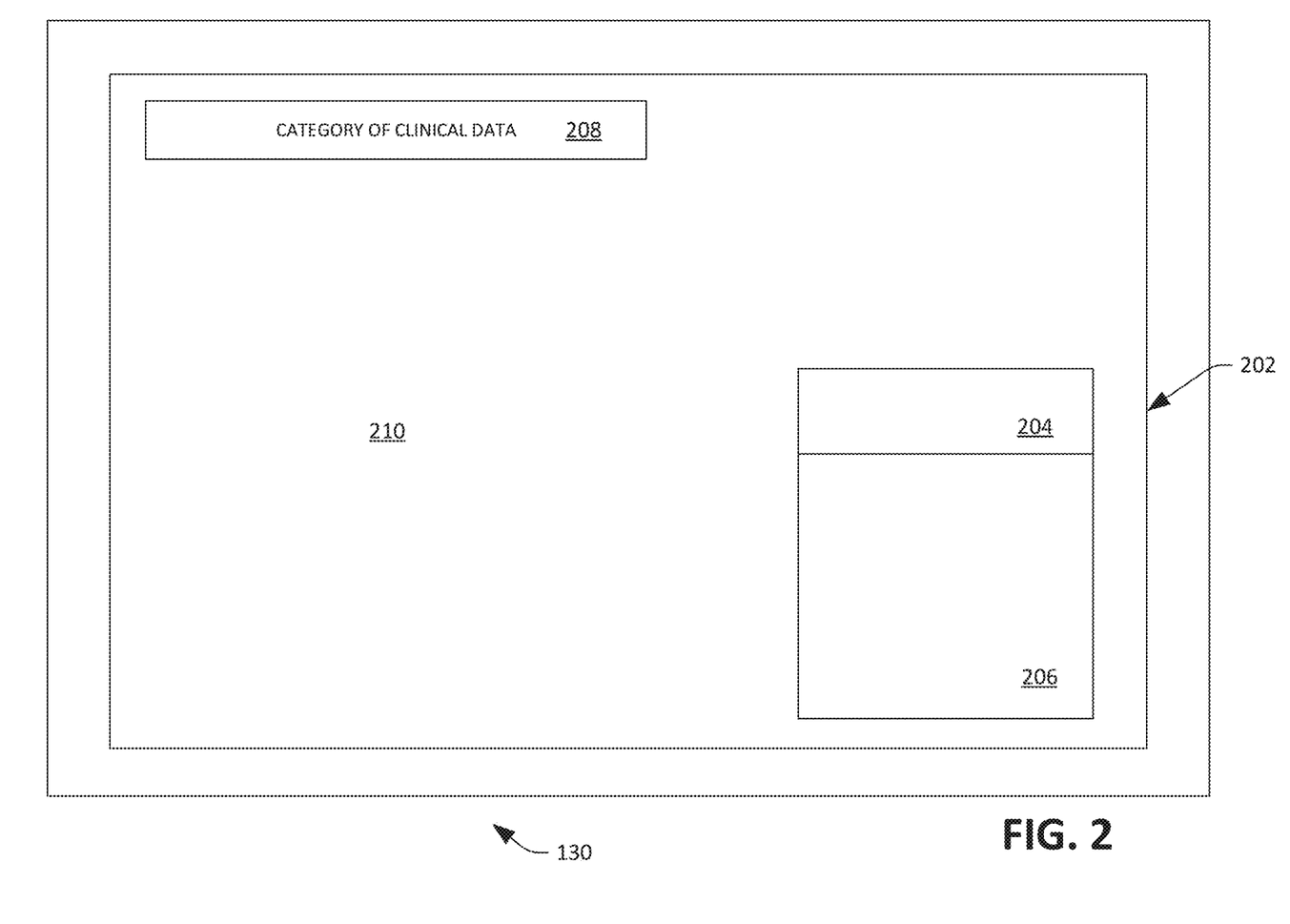
FIG. 2 is an exemplary GUI of a client EHR that is configured to receive data input via a touch-screen display.

Referring now to FIG. 2, an exemplary illustration of the GUI 130 is depicted. The GUI 130 includes a first input field 204, a second input field 206, a category of clinical data field 208, and an electronic health record field 210 that is configured to display at least a portion of an electronic health record of a patient. The first input field 204 is configured to receive free hand input comprising an identifier for a category of clinical data. In an exemplary embodiment, each category of clinical data within an electronic health record is assigned an identifier that identifies the category of clinical data. In a non-limiting example, "Vitals" may be assigned the identifier "V", "Review of Systems" may be assigned the identifier "ROS", and "Family History" may be assigned the identifier "FH".

Subsequent to receiving an identifier for a category at the first input field 204, the client computing device 116 transmits a query to the server EHR 108 for the identified category of clinical data. Responsive to receiving the query, the server EHR 108 searches over the clinical data 112 for the clinical data assigned to the category for the identified patient. The server EHR 108 then transmits search results back to the client EHR 126, which then displays the search results as the portion of the patient's electronic health record in the electronic health record field 210. For example, the first field 204 receives the identifier "V", responsive to which, the client EHR 126 updates the GUI 130 such that the electronic health record field 210 presents clinical data from the "Vitals" category from the patient's electronic health record in the GUI 130 as the portion of the patient's electronic health record. In another example, the first field 204 receives the identifier "ROS", the client EHR 126 updates the GUI 130 such that the electronic health record field 210 presents clinical data from the "Review of Systems" category from the patient's electronic health record on the electronic health record field 210 of the display 202. Responsive to receiving the identifier at the first field 204 and updating the electronic health record field 210 to display the identified portion of the patient's electronic health record, the category of clinical data field 208 also updates to display the name of the category identified.

After the electronic health record field 210 is updated, the second input field 206 receives clinical data of the category of clinical data identified by the input to the first input field 204. For example, if "Vitals" are the identified category of clinical data received by the first input field 204, the clinical data received at the second input field 206 is clinical data for a sub-category of the "Vitals" category (e.g., blood pressure, heart rate, height, weight, etc.). Similarly, if the identified category of clinical data corresponding to the input into the first field 204 is "Family History", the input received at the second input field 206 comprises family history information. Once data of a certain category of clinical data that is to be incorporated into the patient's electronic health record is submitted, the client EHR 126 updates the display 202 to present the next category of clinical data on the electronic health record field 210. Alternatively, the healthcare worker 118 can input the input assigned to the next category of clinical data he or she wishes to enter.

Figure 3:
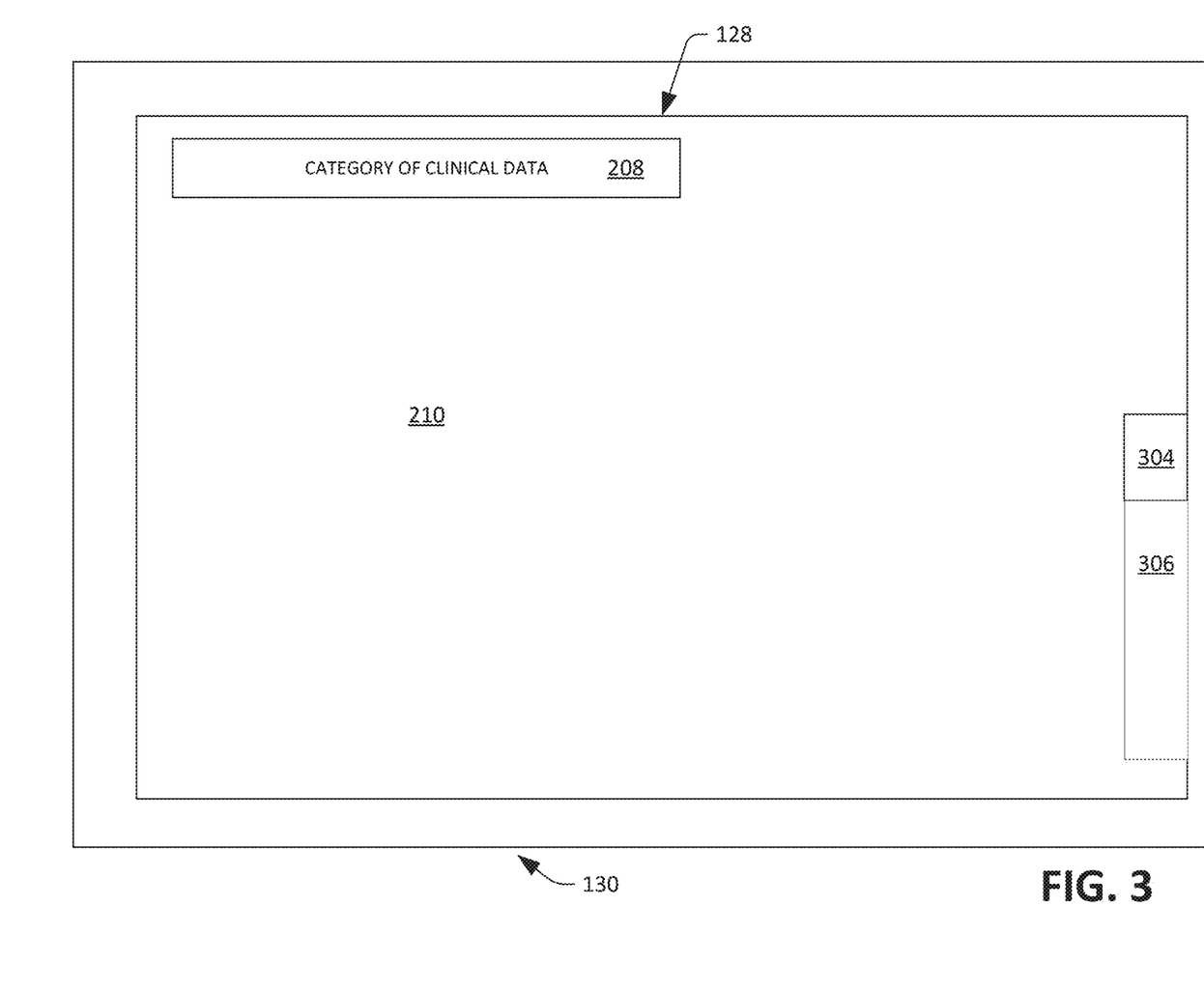
FIG. 3 is an exemplary GUI of a client EHR that is configured to receive data input via a touch-screen display.

Turning now to FIG. 3, an exemplary illustration of the GUI 130 for a client EHR 126 that is presented on the touchscreen display 128 of the client computing device 116 after the client computing device 116 has received a patient's electronic health record from the server computing device 102 is depicted. The GUI 130 of this FIG. 3 depicts a client EHR similar to the GUI 130 of FIG. 2. The GUI 130 includes a display 128, a minimized first input field 304, a minimized second input field 306, the category of clinical data field 208, and the electronic health record field 210. However, unlike the GUI 130 as illustrated in FIG. 2, the first input field 204 and the second input field 206 have been minimized, responsive to a first command received from the healthcare worker 118 by way of the GUI 130, to generate the minimized first input field 304 and the minimized second input field 306. The healthcare worker 118 is able to switch between configurations of the GUI 130 as desired to view clinical data presented in the display 128.

Figure 4:
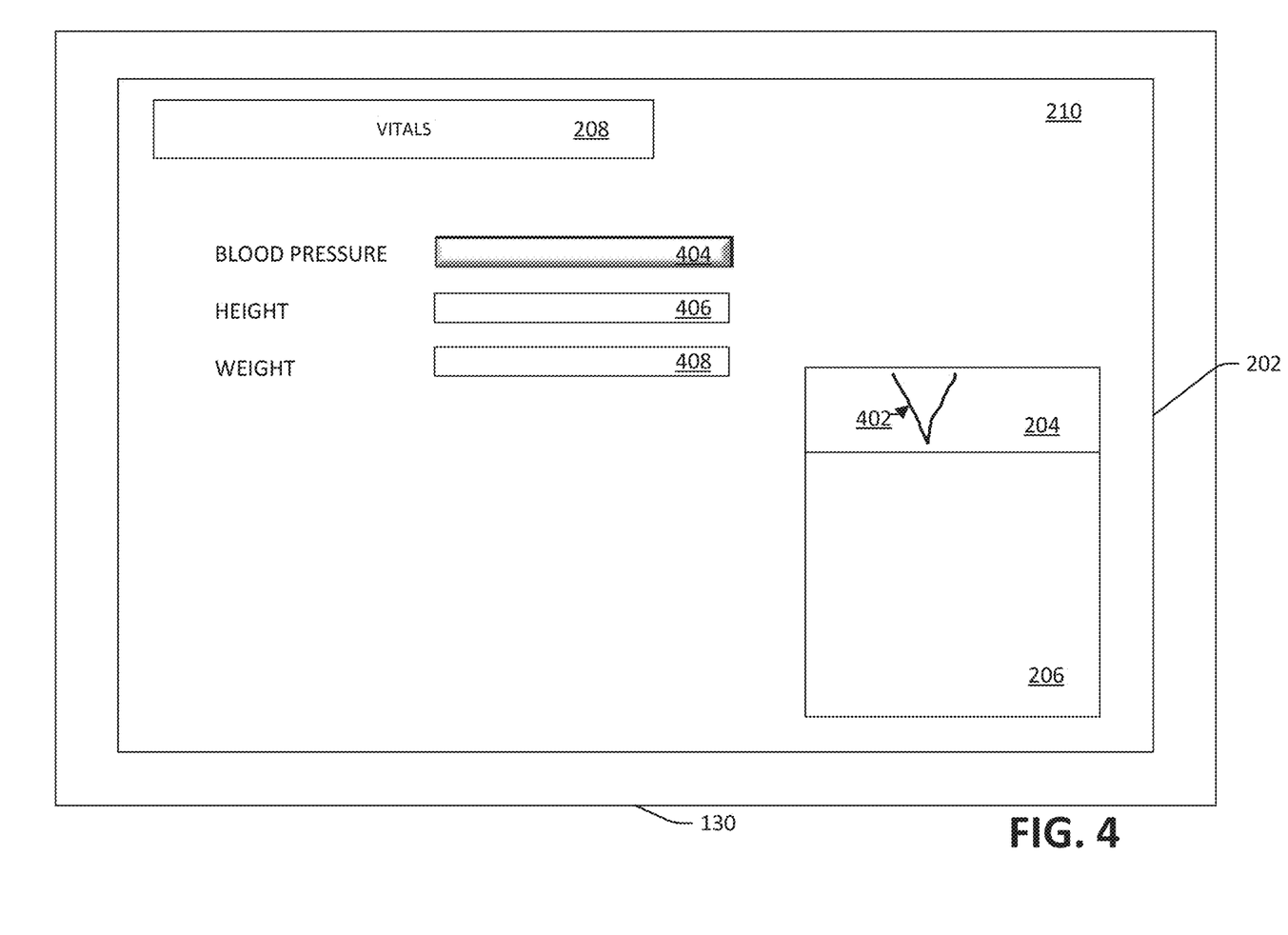
FIG. 4 is an exemplary GUI of a client EHR that is configured to receive data input via a touch-screen display.

Turning now to FIG. 4, an exemplary illustration of the GUI 130 of the client EHR 126 that can be presented on the touchscreen display 128 of the client computing device 116 after the client computing device 116 has received a first identifier 402 at the first input field 204, that identifies a category of data, is depicted. The GUI 130 includes the first input field 204, the second input field 206, the category of clinical data field 208, and the electronic health record field 210. At the first input field 204, FIG. 4 shows an identifier of "V" 402. In this example, the identifier "V" is mapped to the "Vitals" category of clinical data. Responsive to receipt of the identifier, the client EHR 126 updates the category of clinical data field 208 to "Vitals" and populates the electronic health record field 210 with clinical data of the category "Vitals" for the patient. As such, the clinical data displayed on the electronic health record field 210 comprises sub-categories of vitals data, such as blood pressure, height, and weight. These sub-categories comprise data fields, in this exemplary GUI the blood pressure data field 404, the height data field 406, and the weight data field 408 respectively. The blood pressure data field 404 is shown as highlighted because it is where a second input at the second input field 206 will be placed. In this way the healthcare worker 118 can see where the clinical data being provided by way of the GUI 130 will be displayed in the portion of the electronic health record.

Figure 5:
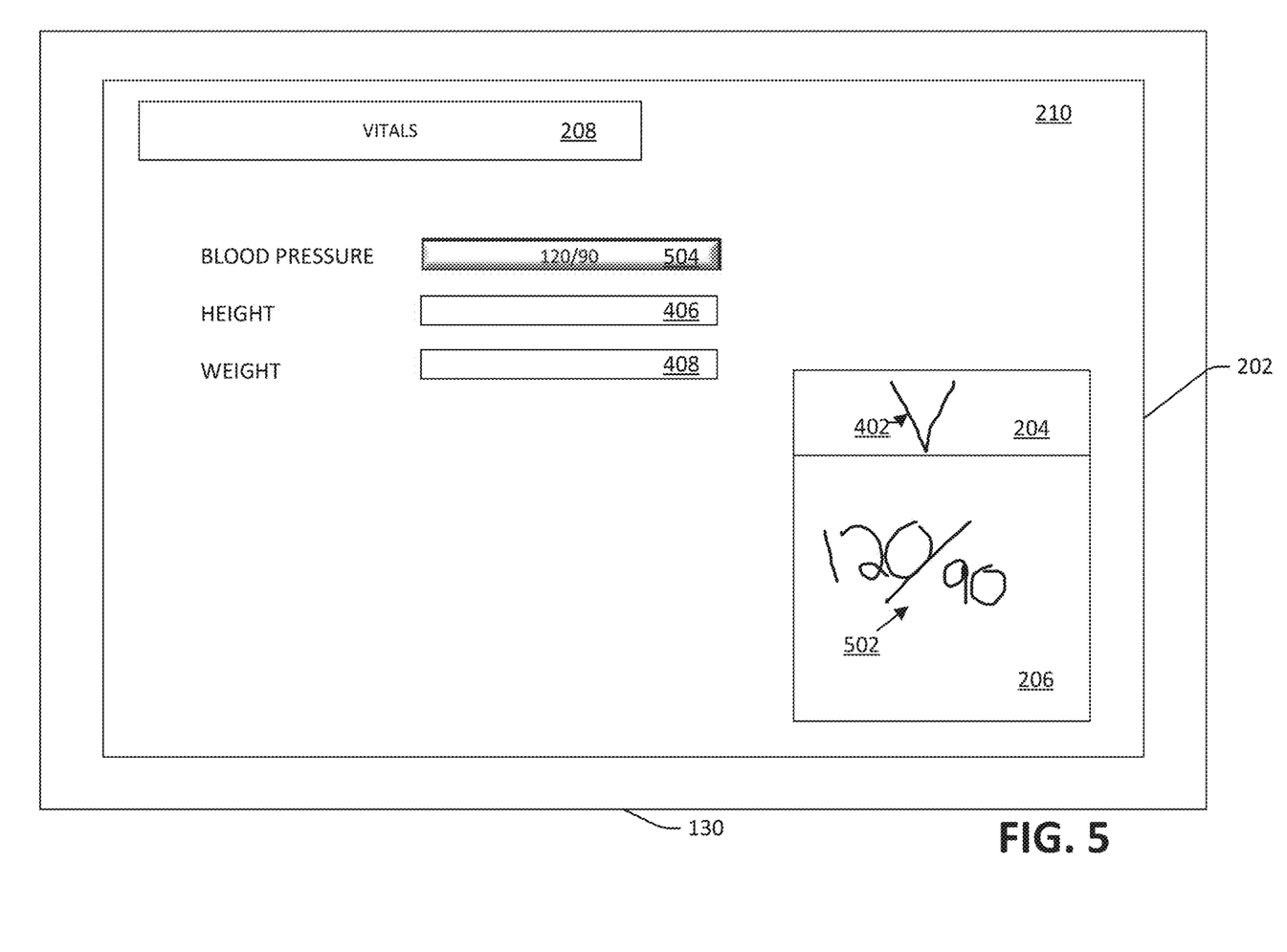
FIG. 5 is an exemplary GUI of a client EHR that is configured to receive data input via a touch-screen display.

Turning now to FIG. 5, an exemplary illustration of the GUI 130 for the client EHR 126 that can be presented on the touchscreen display 128 of the client computing device 116 after the client EHR 126 has received a second identifier, by way of the GUI 130, for a second category of data is depicted. The GUI 130 comprises the first input field 204, the second input field 206, the category of clinical data field 208, and the electronic health record field 210, wherein the electronic health record field 210 displays vitals information based on the identifier "V" 402 discussed above with regard to FIG. 4. The first appearing subcategory of the vitals category is blood pressure. At the second input field 206, FIG. 5 depicts the client EHR 126 receiving a first clinical data entry 502 comprising "120/90". Responsive to receiving the first clinical data entry 502, the client EHR 126 updates the blood pressure data field 504 to populate it with digitized input of "120/90" 504 based on the first clinical data entry 502. Responsive to receiving the first clinical data entry 502 for the blood pressure data field 504, the client EHR 126 updates the GUI 130 to highlight (not depicted) the height data field 406 to indicate that the next entry of clinical data received will populate the height data field 406 unless the client EHR 126 receives other instructions.

Figure 6:
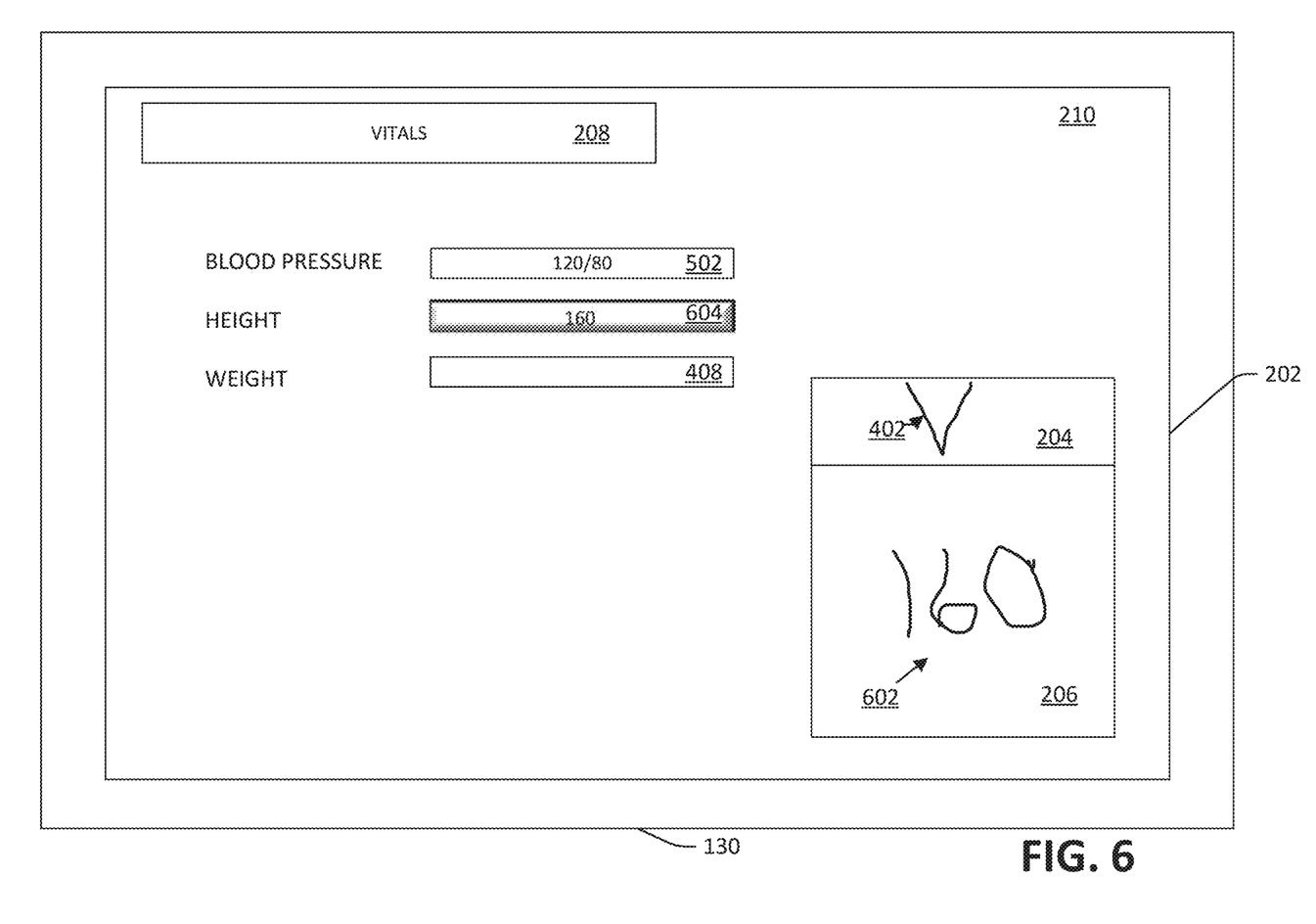
FIG. 6 is an exemplary GUI of a client EHR that is configured to receive data input via a touch-screen display.

Turning now to FIG. 6, an exemplary illustration of the GUI 130 for the client EHR 126 that can be presented on the touchscreen display 128 of the client computing device 116 after the client EHR 126 has received the first clinical data entry 502 at the second input field 206 is depicted. The GUI 130 comprises the first input field 204, the second input field 206, the category of clinical data field 208, and the electronic health record field 210 wherein the electronic health record field 210 is displaying vitals information based on the identifier "V" 402 discussed above with regard to FIG. 4. Additionally, the blood pressure data field 504 is displaying the first clinical data entry 502 comprising the text of "120/80" 502 previously received from the healthcare worker 118 by way of the GUI 130. At the second input field 206, FIG. 6 shows a second clinical data entry 602 comprising "160". Responsive to receipt of the second clinical data entry 602, the client EHR 126 updates the height data field 504 to populate it with text of "160" 604 based on the second clinical data entry 602. Responsive to receiving the second clinical data entry 602 for the height data field 504, the client EHR 126 updates the GUI 130 to highlight (not depicted) the weight data field 408 to indicate that the next clinical data entry received will populate the weight data field 408 unless the client EHR 126 receives other instructions.

Figure 7:
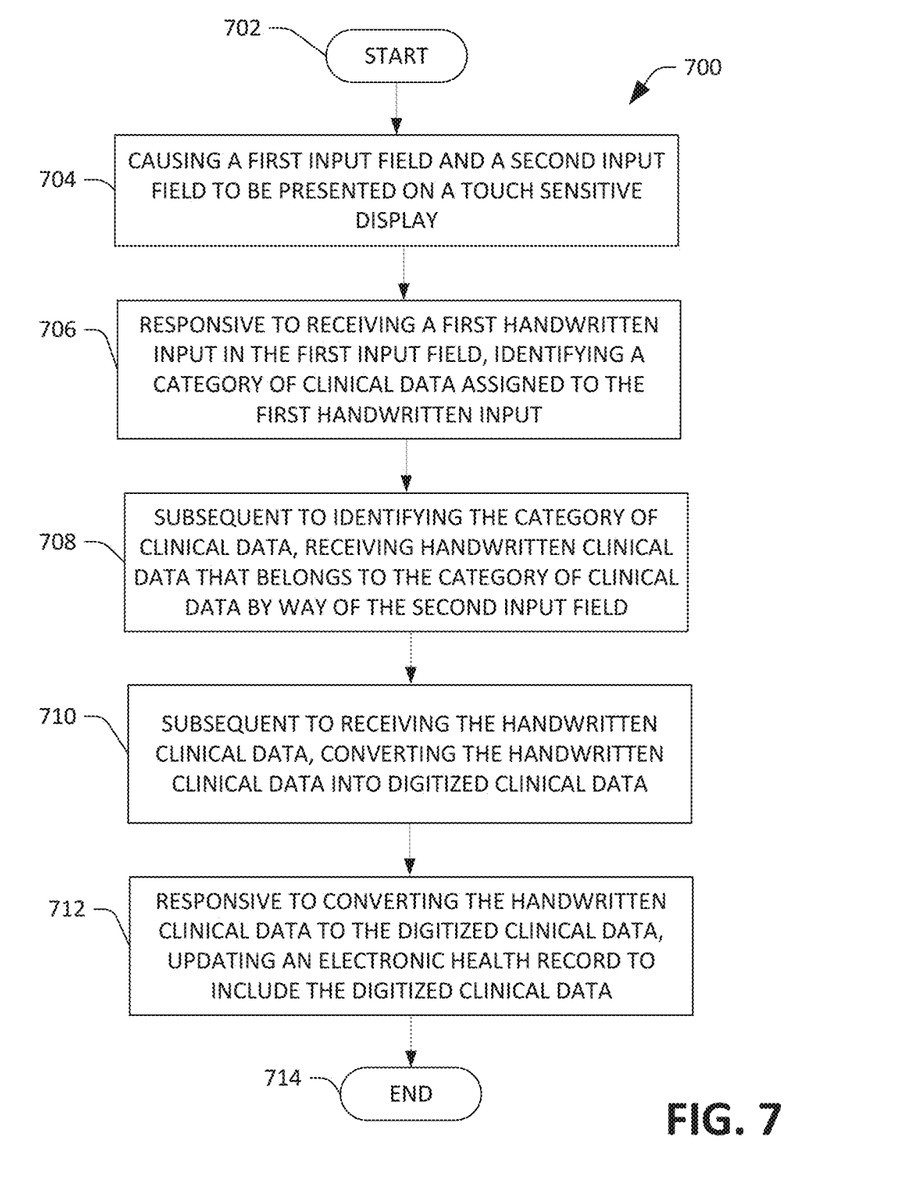
FIG. 7 is a flow diagram illustrating an exemplary methodology that facilitates updating an electronic health record of a patient.
Figure 8:
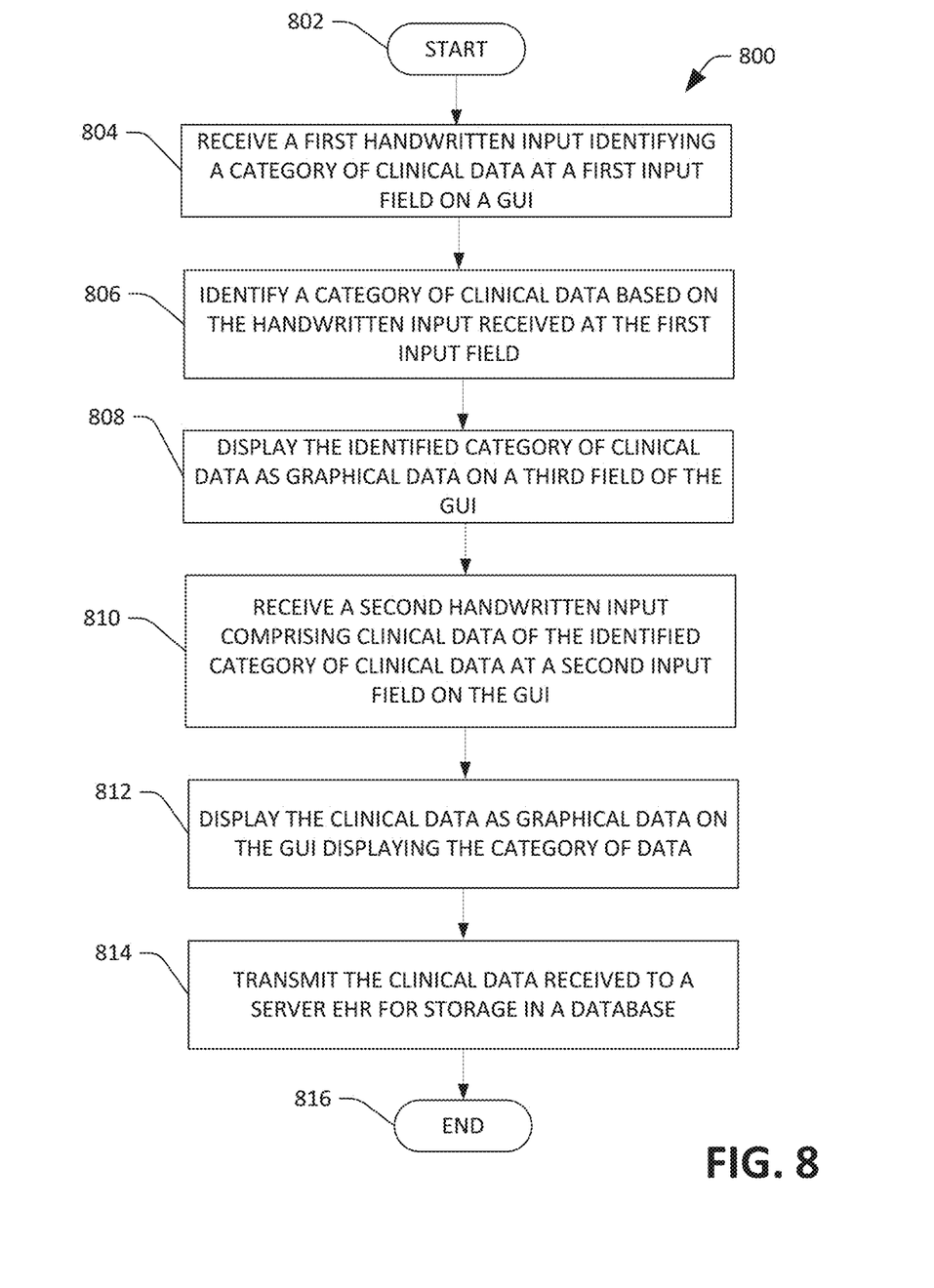
FIG. 8 is a flow diagram illustrating an exemplary methodology that facilitates updating an electronic health record of a patient.
Figure 9:
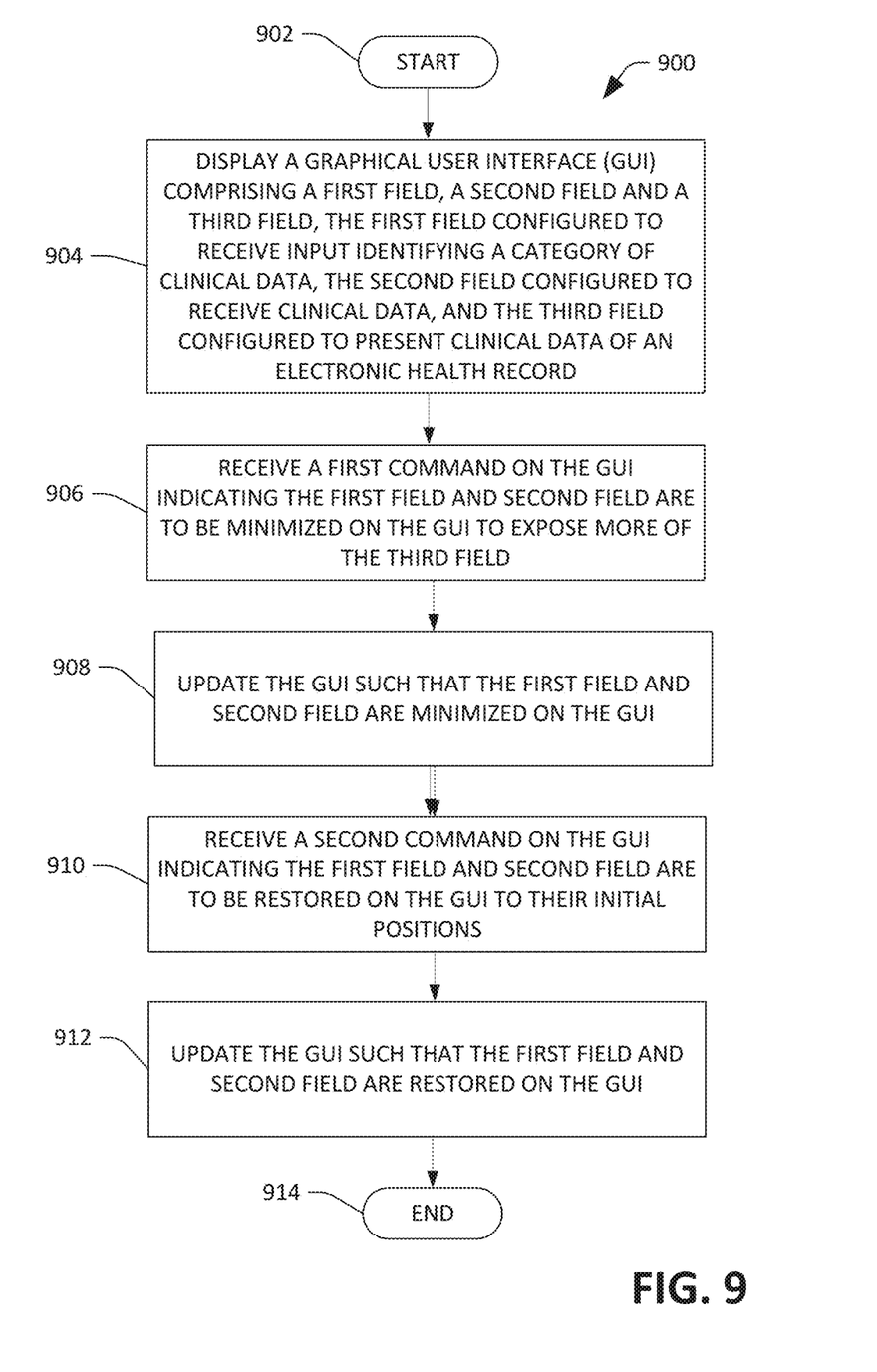
FIG. 9 is a flow diagram illustrating exemplary methodology that facilitates data entry at a GUI within a client EHR.

FIGS. 7-9 illustrate exemplary methodologies relating to a graphical user interface configured for data entry. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Turning now to FIG. 7, a methodology 700 executed by a client computing device that facilitates data entry in a GUI of a client EHR is illustrated. The methodology 700 begins at 702, and at 704, the client EHR causes a first input field and a second input field to be presented on a touch sensitive display of the client computing device. At 706, the client EHR identifies the category of data assigned to an identifier received as first handwritten input by way of the first input field. For instance, the category could be "Review of Systems", "Vitals", "Medications", "Family History", etc. The identifier can be entered on the touch sensitive display using a soft keyboard, a stylus, a finger, or the like. The identifier is assigned to a category of clinical data within an electronic health record of a patient. The identifier can comprise any predefined sequence of alphanumeric characters. At 708, the client EHR receives handwritten clinical data that belongs to a second category of clinical data by way of the second input field. The handwritten clinical data can comprise any clinical data of the patient that is being entered by a healthcare worker. At 710, the client EHR converts the handwritten clinical data into digitized clinical data capable of being displayed on the GUI and integrated into the patient's electronic health record. At 712, responsive to converting the handwritten clinical data into the digitized clinical data, the electronic health record is updated to include the digitized clinical data. The digitized clinical data is then to be stored in a data store as part of the patient's electronic health record along with all of the other clinical data associated with the patient. The methodology 700 concludes at 714.

Turning now to FIG. 8, a methodology 800 executed by a server computing device that facilitates generating a GUI for a client EHR is illustrated. The methodology 800 begins at 802, and at 804, a client EHR executing on a client computing device receives a first handwritten input at a first input field on the GUI of the client EHR, wherein the first handwritten input comprises an identifier for a category of clinical data. The GUI further comprises a second input field and a third input field, wherein the second input field is configured to receive input comprising clinical data about the patient and the third input field is configured to display at least a portion of an electronic health record of the patient. At 806, the client EHR identifies a category of clinical data based upon the identifier received at the first input field. For example, if the first input field receives an identifier comprising "ROS", the client EHR can recognize that "ROS" is mapped to "Review of Systems". At 808, based on the identified category, a server EHR in network communication with the client EHR executes a search over a database maintained by the server EHR for clinical data of the patient. The server EHR transmits the clinical data indexed to the patient to the client EHR, which then presents the identified category of clinical data of the patient on the third field of the GUI. At 810, the client EHR receives second handwritten input comprising clinical data of the identified category of clinical data at the second input field on the GUI. Subsequently, at 812, the client EHR updates the display to include the clinical data received as graphical data on the GUI. At 814, responsive to receiving the entered clinical data of the identified category type, transmitting the entered clinical data to the server EHR for storage in a data store maintained by the server EHR as part of the patient's electronic health record. The methodology 800 concludes at 816.

Turning now to FIG. 9, a methodology 900 executed by a client computing device that facilitates generating a GUI for a client EHR is illustrated. The methodology 900 begins at 902, and at 904, a client EHR application executing on a client computing device presents a GUI comprising a first field configured to receive input identifying a category of clinical data, a second field configured to receive clinical data, and a third field configured to present clinical data within a patient's electronic health record. At 906, the GUI receives a first command from a healthcare worker indicating the first field and the second field are to be minimized on the display thereby exposing more of the third field of the GUI. At 908, the client EHR updates the GUI such that the first field and the second field are minimized exposing more of the third field which is configured to display clinical data from a patient's electronic health record. In effect, minimizing the first and second field allows the healthcare worker interacting with the client computing device to review more of the patient's clinical data without further interactions with the GUI. At 910, the client EHR receives a second command from the healthcare worker 118 by way of the GUI indicating the first field and the second field are to be restored to their initial positions on the GUI once more obscuring portions of the electronic health record. At 912, the client EHR updates the GUI such that the first field and the second field are restored to their initial position on the GUI. The methodology 900 concludes at 914.

Figure 10:
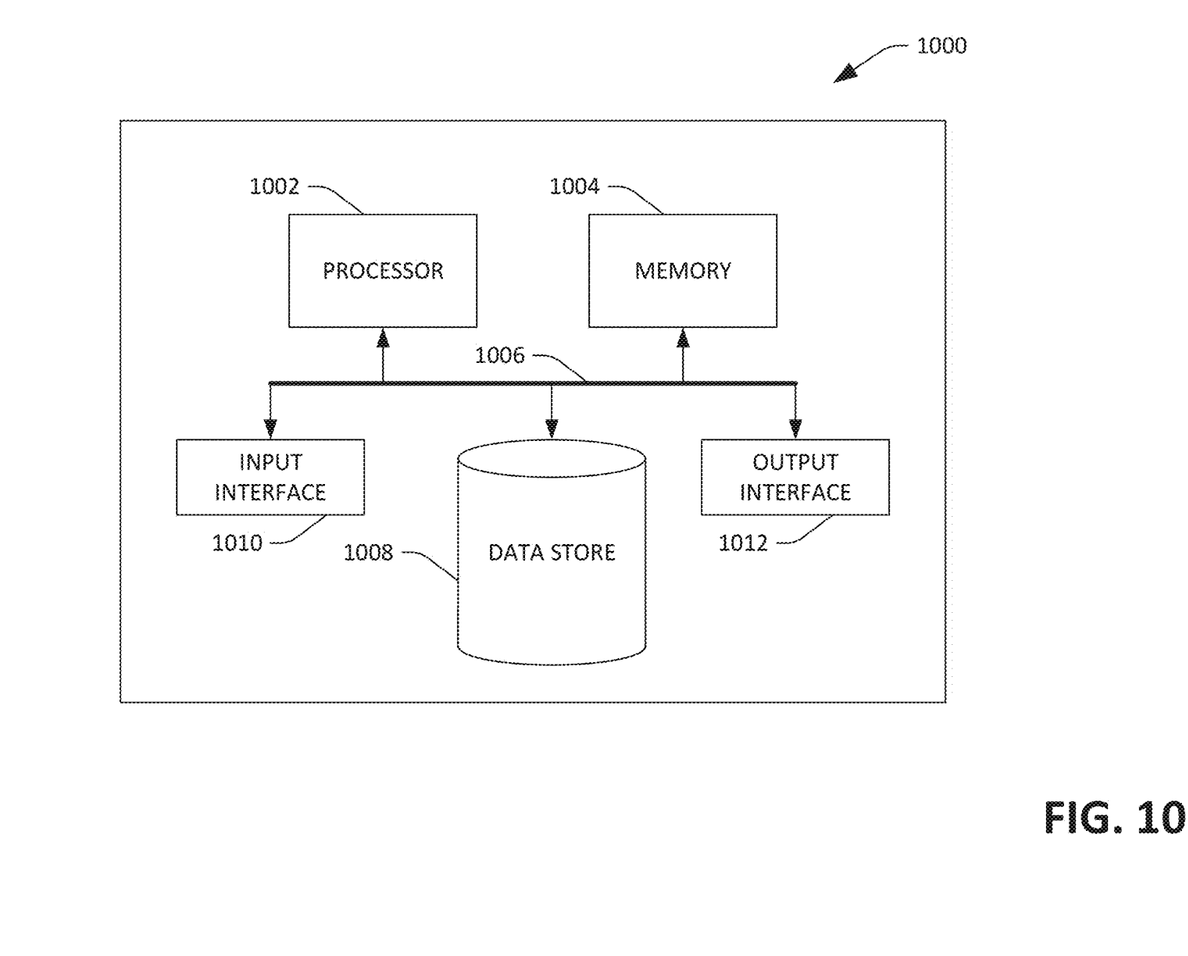
FIG. 10 is an exemplary computing system.

Referring now to FIG. 10, a high-level illustration of an exemplary computing device 1000 that can be used in accordance with the systems and methodologies disclosed herein is illustrated. For instance, the computing device 1000 may be used in a system that facilitates efficient data entry of clinical data on a tablet computing device. By way of another example, the computing device 1000 can be used in a system that receives and stores clinical data regarding a patient using a specialized data entry field on a GUI of the computing device 1000. The computing device 1000 includes at least one processor 1002 that executes instructions that are stored in a memory 1004. The instructions may be, for instance, instructions for implementing functionality described as being carried out by one or more components discussed above or instructions for implementing one or more of the methods described above. The processor 1002 may access the memory 1004 by way of a system bus 1006. In addition to storing executable instructions, the memory 1004 may also store clinical data, sequence data, etc.

The computing device 1000 additionally includes a data store 1008 that is accessible by the processor 1002 by way of the system bus 1006. The data store 1008 may include executable instructions, clinical data, category data, etc. The computing device 1000 also includes an input interface 1010 that allows external devices to communicate with the computing device 1000. For instance, the input interface 1010 may be used to receive instructions from an external computer device, from a user, etc. The computing device 1000 also includes an output interface 1012 that interfaces the computing device 1000 with one or more external devices. For example, the computing device 1000 may display text, images, etc. by way of the output interface 1012.

It is contemplated that the external devices that communicate with the computing device 1000 via the input interface 1010 and the output interface 1012 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 1000 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 1000 may be a distributed system. Thus, for instance, several devices may be in communication by way of a network connection and may collectively perform tasks described as being performed by the computing device 1000.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A client computing device comprising:
   a processor;
   a touch-sensitive display that is operably coupled to the processor; and
   memory storing a client electronic health record application (EHR) that, when executed by the processor, causes the processor to perform acts comprising:
   causing a graphical user interface (GUI) of the client EHR to be displayed on the touch-sensitive display, wherein the GUI comprises a first input field and a second input field;
   receiving, by way of the first input field, a handwritten identifier for a category of clinical data;
   responsive to receiving the handwritten identifier and based upon the handwritten identifier, identifying the category of clinical data assigned to the handwritten identifier;
   subsequent to identifying the category of clinical data that is assigned to the received handwritten identifier, receiving, by way of the second input field, handwritten clinical data that belongs to the category, wherein the handwritten clinical data is for a patient;
   converting the handwritten clinical data to digitized clinical data; and
   responsive to converting the handwritten clinical data to the digitized clinical data, transmitting the digitized clinical data to a server computing device that is in network communication with the client computing device, wherein an electronic health record of the patient is updated to include the digitized clinical data, and further wherein the digitized clinical data is assigned to the category of clinical data in the electronic health record of the patient.

2. The client computing device of claim 1, wherein the GUI includes a third field, wherein the third field is configured to present a portion of the electronic health record.

3. The client computing device of claim 2, the acts further comprising presenting the digitized clinical data in the third field.

4. The client computing device of claim 3, wherein the GUI comprises a fourth field, wherein the fourth field is assigned to a sub-category of the category, and further wherein the fourth field is selected, the acts further comprising:
   responsive to converting the handwritten clinical data to the digitized clinical data, displaying the digitized clinical data in the third field, wherein the digitized clinical data is assigned to the sub-category of the category in the electronic health record.

5. The client computing device of claim 4, wherein the GUI comprises a fifth field that is assigned a second-sub-category of the category, the acts further comprising:
   prior to causing the electronic health record to be updated to include the digitized clinical data, receiving a command that indicates that the electronic health record is to be updated to include the digitized clinical data;
   responsive to receiving the command, selecting the fifth field;
   receiving the second handwritten clinical data in the second field of the GUI;
   responsive to receiving the second handwritten clinical data in the second field of the GUI, converting the second handwritten clinical data to second digitized clinical data; and
   entering the second digitized clinical data into the fifth field.

6. The client computing device of claim 1, the acts further comprising:
   receiving a request to display a virtual keyboard on the touch-sensitive display; and
   responsive to receiving the request, displaying the virtual keyboard on the touch-sensitive display and removing the first field and the second field from the GUI.

7. The client computing device of claim 1, the acts further comprising:
   receiving a second handwritten identifier in the first field of the GUI, the second handwritten identifier being for a second category; and
   updating the GUI to present data related to the second category.

8. A method performed by a client computing device, wherein the client computing device comprises a processor, a touch-sensitive display, and memory, wherein the memory stores a client electronic health records application (client EHR), and further wherein the client computing device performs the method when the processor executes the client EHR, the method comprising:
   causing a graphical user interface (GUI) of the client EHR to be displayed on the touch-sensitive display, wherein the GUI comprises a first input field and a second input field;
   receiving, by way of the first input field, a handwritten identifier for a category of clinical data;
   responsive to receiving the handwritten identifier and based upon the handwritten identifier, identifying the category of clinical data assigned to the handwritten identifier;
   subsequent to identifying the category of clinical data that is assigned to the handwritten identifier, receiving, by way of the second input field, handwritten clinical data that belongs to the category, wherein the handwritten clinical data is for a patient;
   converting the handwritten clinical data to digitized clinical data; and
   responsive to converting the handwritten clinical data to the digitized clinical data, transmitting the digitized clinical data to a server computing device that is in network communication with the client computing device, wherein an electronic health record to of the patient is updated to include the digitized clinical data, and further wherein the digitized clinical data is assigned to the category of clinical data in the electronic health record of the patient.

9. The method of claim 8, wherein the GUI includes a third field, wherein the third field is configured to present a portion of the electronic health record.

10. The method of claim 9, further comprising presenting the digitized clinical data in the third field.

11. The method of claim 10, wherein the GUI comprises a fourth field, wherein the fourth field is assigned to a sub-category of the category, and further wherein the fourth field is selected, the method further comprising:
responsive to converting the handwritten clinical data to the digitized clinical data, displaying the digitized clinical data in the third field, wherein the digitized clinical data is assigned to the sub-category of the category in the electronic health record.

12. The method of claim 11, wherein the GUI comprises a fifth field that is assigned a second-sub-category of the category, the method further comprising:
prior to causing the electronic health record to be updated to include the digitized clinical data, receiving a command that indicates that the electronic health record is to be updated to include the digitized clinical data;
responsive to receiving the command, selecting the fifth field;
receiving the second handwritten clinical data in the second field of the GUI;
responsive to receiving the second handwritten clinical data in the second field of the GUI, converting the second handwritten clinical data to second digitized clinical data; and
entering the second digitized clinical data into the fifth field.

13. The method of claim 8, further comprising:
receiving a request to display a virtual keyboard on the touch-sensitive display; and
responsive to receiving the request, displaying the virtual keyboard on the touch-sensitive display and removing the first field and the second field from the GUI.

14. The method of claim 8, further comprising:
receiving a second handwritten identifier in the first field of the GUI, the second handwritten identifier being for a second category; and
updating the GUI to present data related to the second category.

15. A computer-readable storage medium of a client computing device that is operated by a clinician, the computer-readable storage medium comprising a client electronic health records application (client EHR), wherein the client EHR, when executed by a processor, causes the processor to perform acts comprising:
causing a graphical user interface (GUI) of the client EHR to be displayed on the touch-sensitive display, wherein the GUI comprises a first input field and a second input field;
receiving, from the clinician and by way of the first input field, a handwritten identifier for a category of clinical data;
responsive to receiving the handwritten identifier, identifying the category of clinical data assigned to the handwritten identifier;
subsequent to identifying the category of clinical data, receiving, from the clinician and by way of the second input field, handwritten clinical data that belongs to the category, the handwritten clinical data set forth by the clinician with respect to a patient of the clinician;
converting the handwritten clinical data to digitized clinical data; and
responsive to converting the handwritten clinical data to the digitized clinical data, transmitting the digitized clinical data to a server computing device that is in network communication with the client computing device, wherein an electronic health record of the patient is updated by the server computing device to include the digitized clinical data, and further wherein the digitized clinical data is assigned to the category of clinical data in the electronic health record of the patient.

16. The computer-readable storage medium of claim 15, wherein the GUI includes a third field, wherein the third field is configured to present a portion of the electronic health record.

17. The computer-readable storage medium of claim 16, the acts further comprising presenting the digitized clinical data in the third field.

18. The computer-readable storage medium of claim 17, wherein the GUI comprises a fourth field, wherein the fourth field is assigned to a sub-category of the category, and further wherein the fourth field is selected, the acts further comprising:
responsive to converting the handwritten clinical data to the digitized clinical data, displaying the digitized clinical data in the third field, wherein the digitized clinical data is assigned to the sub-category of the category in the electronic health record.

19. The computer-readable storage medium of claim 18, wherein the GUI comprises a fifth field that is assigned a second-sub-category of the category, the acts further comprising:
prior to causing the electronic health record to be updated to include the digitized clinical data, receiving a command that indicates that the electronic health record is to be updated to include the digitized clinical data;
responsive to receiving the command, selecting the fifth field;
receiving the second handwritten clinical data in the second field of the GUI;
responsive to receiving the second handwritten clinical data in the second field of the GUI, converting the second handwritten clinical data to second digitized clinical data; and
entering the second digitized clinical data into the fifth field.

20. The computer-readable storage medium of claim 16, the acts further comprising:
receiving a request to display a virtual keyboard on the touch-sensitive display; and
responsive to receiving the request, displaying the virtual keyboard on the touch-sensitive display and removing the first field and the second field from the GUI.

* * * * *